United States Patent
Newbound

(10) Patent No.: US 6,920,802 B2
(45) Date of Patent: Jul. 26, 2005

(54) ADSORPTION TRAP FOR THE DETECTION OF SURFACE-ACTIVE AGENTS IN GAS STREAMS

(75) Inventor: Timothy Dale Newbound, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 10/132,763

(22) Filed: Apr. 24, 2002

(65) Prior Publication Data

US 2003/0200788 A1 Oct. 30, 2003

(51) Int. Cl.[7] .......................... G01N 1/00; B01N 59/26
(52) U.S. Cl. .................... 73/863.23; 73/863.24; 73/863.25; 73/31.03; 96/138
(58) Field of Search .............. 73/863.12, 863.21, 73/863.22, 863.23, 863.24, 863.25, 31.03, 23.41, 29.02, 29.05; 96/138, 108; 146/46.1; 208/237, 299

(56) References Cited

U.S. PATENT DOCUMENTS

| | | | | |
|---|---|---|---|---|
| 2,119,288 A | * | 5/1938 | Raymond | 73/863.23 |
| 2,845,138 A | * | 7/1958 | Gageby | 96/151 |
| 3,507,147 A | * | 4/1970 | Llewellyn | 73/23.36 |
| 3,834,130 A | * | 9/1974 | Bissada et al. | 96/126 |
| 3,897,679 A | * | 8/1975 | Guild | 73/61.52 |
| 4,046,014 A | * | 9/1977 | Boehringer et al. | 73/863.12 |
| 4,197,098 A | * | 4/1980 | Stiehl et al. | 96/110 |
| 4,367,645 A | * | 1/1983 | Froment | 73/23.38 |
| 4,382,808 A | * | 5/1983 | Van Wormer et al. | 55/418 |
| 4,621,518 A | * | 11/1986 | Gerdes | 73/23.35 |
| 5,059,405 A | * | 10/1991 | Watson et al. | 423/210 |
| 5,142,143 A | * | 8/1992 | Fite et al. | 73/863.12 |
| 5,571,944 A | * | 11/1996 | Pfeifer et al. | 73/24.04 |
| 5,574,230 A | * | 11/1996 | Baugh | 73/863.23 |
| 5,667,566 A | * | 9/1997 | Flynn et al. | 96/117.5 |
| 5,759,485 A | * | 6/1998 | Fischer et al. | 422/16 |
| 5,792,897 A | * | 8/1998 | Rosser et al. | 585/738 |
| 5,919,354 A | * | 7/1999 | Bartek | 208/299 |
| 6,477,905 B1 | * | 11/2002 | Mitra | 73/863.12 |
| 2001/0029775 A1 | * | 10/2001 | Uchihara et al. | 73/28.01 |
| 2002/0112992 A1 | * | 8/2002 | Johnson et al. | 208/305 |
| 2003/0106840 A1 | * | 6/2003 | Franco et al. | 208/245 |

FOREIGN PATENT DOCUMENTS

EP        438036 A2 * 12/1990

OTHER PUBLICATIONS

Web page, http://www.petroleum-analyzer.com/product/PSPIlab/wettest.htm , copyright 2001, no month.*

* cited by examiner

Primary Examiner—Michael Cygan
(74) Attorney, Agent, or Firm—Abelman, Frayne & Schwab

(57) ABSTRACT

A method and apparatus are provided for adsorbing surface-active compounds, such as corrosion inhibitors and water, from pressurized gas streams utilizing existing gas pipeline sampling valves. The apparatus includes an adsorption trap assembly containing an adsorption material packing, such as silica gel, fixedly positioned to selectively adsorb any surface-active compound(s) or water in the gas stream passing through the trap. After sampling, the adsorption material packing is removed and treated to desorb any entrained compound(s) for recovery, testing and identification. The method and apparatus have particular utility in determining the presence of corrosion inhibitors that have been added to petroleum pipelines upstream of the sampling point(s).

39 Claims, 7 Drawing Sheets

ADSORPTION TRAP FOR THE DETECTION OF SURFACE-ACTIVE AGENTS IN GAS STREAMS

FIELD OF THE INVENTION

The present invention relates to methods and apparatus for sampling gas streams to determine the presence of moisture or corrosion inhibitors, specifically imidazoline-type inhibitors, in gas pipelines and, more particularly, to a method and apparatus for sampling sour gas streams for the presence of corrosion inhibitor residue in order to optimize the upstream injection rates of the corrosion inhibitor and to determine its effectiveness.

BACKGROUND OF THE INVENTION

It is well known in the art that corrosive elements and related contaminants are present in pipelines used for transporting sweet and sour hydrocarbon gases downstream of gas-oil separation plants. Corrosive contaminants are damaging to metal equipment, and more particularly to steel pipelines and fittings. Hydrocarbon pipelines cover substantial distances worldwide. Therefore, corrosion protection of these lines is of vital importance, especially in heavily populated and environmentally sensitive regions. Damage to pipelines by corrosive elements can result in catastrophic disasters culminating in losses of human life and substantial injury to the environment, in addition to extreme economic loss. Therefore, it is essential that the presence of corrosive elements in such pipelines be carefully monitored and neutralized by the addition of effective amounts of corrosion inhibitors.

Monitoring corrosion inhibitors transported over long distances in pressurized gas pipelines has proven to be a challenging task. Computer simulation program models have been developed and implemented to simulate and predict the transport properties of inhibitor compounds and solutions employed for treating and neutralizing corrosive elements across pipeline distances. Although these simulation programs have proved useful, analytical sampling is still necessary for verification of the presence of effective amounts of corrosion inhibitors and their derivatives. However, conventional sampling for analysis has also proved to be difficult in sour gas pipelines based on limited access to sampling points.

Various methods, techniques and chemicals have been developed for removing or minimizing the effects of corrosive substances in sour gas lines. As used herein, the term effective amount of corrosion inhibitor, such as imidazoline and/or its derivatives, is that amount necessary to eliminate or keep to an acceptable minimum corrosion of the pipeline and its fittings. Specific methods for removing water and sulfur-based compounds are disclosed in the art. For example, Nivens, et al. U.S. Pat. No. 4,011,882 discloses a method for minimizing sulfur contamination of refined hydrocarbon fluids transported in a pipeline for the transportation of sweet and sour hydrocarbon fluids by first mixing a corrosion inhibitor with a sour hydrocarbon and transporting the mixture through the a pipeline. The sour mixture is subsequently followed by a sweet hydrocarbon wash solution including amines. Finally, a refined hydrocarbon fluid is transported through the pipeline.

Roe U.S. Pat. No. 6,063,288 teaches a method for controlling the deposition of silicate and silica-containing scales in an aqueous system comprising the addition of an imidazoline or imidazoline derivative to control scale deposits on the surfaces contacted by the aqueous system. Roe is limited to the interaction of silicate and silica with imidazoline and imidazoline derivatives in industrial applications such as cooling and boiler water systems.

Knox et al. U.S. Pat. No. 4,927,669 discloses an inhibitor formulation including the product obtained by reacting maleic anhydride or fumaric acid with fatty acids containing unsaturation in the presence of a suitable catalyst, such as iodine, clay or silica. The disclosure in Knox purports to provide improved corrosion inhibition in oil field equipment and piping over conventional dimer/trimer based inhibitor formulations.

Alford et al. U.S. Pat. No. 5,174,913 discloses a corrosion inhibitor with improved film forming and film persistency characteristics produced by first reacting, in a condensation reaction, a polybasic acid with a polyalcohol to form a partial ester. Next, the partial ester is reacted with imidazoline and/or fatty diamines to salt the ester. Alford further teaches of reacting the slated ester with a metal hydroxide, a metal oxide, and/or ammonia to further salt the ester. In addition, surfactants may be added to tailor the inhibitor formulation to meet the specific needs of the user.

Poirier et al. U.S. Pat. No. 5,199,978 discloses a process for removing elemental sulfur from fluids such as gasoline, diesel fuel, jet fuel or octane enhancement additives such as ethers (MTBE) which pick up sulfur when transported through pipelines which are otherwise used for the transport of sour hydrocarbon streams. Sulfur containing fluids are mixed with an inorganic caustic material, an alkyl alcohol and an organic mercaptan or inorganic sulfide compound capable of reacting with sulfur to form a fluid insoluble polysulfide salt reaction product at ambient reaction temperatures. The treated fluid is then contacted with an adsorbent or filtered to remove the insoluble salt leaving a fluid product of very low residual sulfur content.

Fischer et al. U.S. Pat. No. 5,292,480 discloses a corrosion inhibitor with excellent film forming and film persistency characteristics. The corrosion inhibitor in Fischer is produced by first reacting unsaturated fatty acids with maleic anhydride or fumaric acid to produce the fatty acid Diels-Alder adduct or the fatty acid-one reaction product. The adduct or reaction product is further reacted in a condensation or hydrolysation reaction with a polyalcohol to form an acid-anhydride ester corrosion inhibitor. The ester may be reacted with amines, metal hydroxides, metal oxides, ammonia, and combinations thereof to neutralize the ester.

Gillespie et al. U.S. Pat. No. 5,389,240 discloses a method for removing naphthionic acids. Naphthionic acids may be removed from liquid hydrocarbon feedstocks by passing such feedstocks through a bed of certain metal oxide solid solutions related to hydrotalcites. The removal of naphthionic acids is an important adjunct to sweetening sour feedstocks and is particularly applicable to kerosines whose acid numbers may range as high as about 0.8.

Ferm et al. U.S. Pat. No. 5,401,390 discloses a catalyst and a process for using the catalyst disclosed. The catalyst is a metal chelate dispersed on a basic support which is a combination of a solid base and a secondary component. The solid base can be a solid solution of metal oxides and/or a layered double hydroxide (LDH) and the secondary component can be calcium oxide, magnesium oxide, calcium hydroxide and magnesium hydroxide. The process involves contacting a sour hydrocarbon fraction which contains mercaptans with the catalyst in the presence of an oxidizing agent and a polar compound.

Falkiner et al. U.S. Pat. No. 5,525,233 discloses a process for removing elemental sulfur from fluids such as refined petroleum products transported through pipelines normally used for the transport of sour hydrocarbon streams. The sulfur containing fluids are mixed with an immiscible aliphatic solution containing an inorganic caustic material, methanol or aqueous alcohol and an inorganic sulfide or hydrosulfide capable of reacting with the elemental sulfur in a mixing zone to form a polysulfide present in the immiscible alcoholic solution.

Fischer et al. U.S. Pat. No. 5,759,485 discloses water-soluble corrosion inhibiting compositions and the method of making the same. Specifically, this invention relates to inhibiting the corrosion of metals, particularly those employed in the production, processing, and transportation of petrochemical products. These water-soluble corrosion inhibiting compositions are created by neutralizing a tricarboxylic acid with aminoethylethanolamine and a member selected from the group consisting of imidazoline, amidoamine, and combinations thereof. The resulting compositions exhibit improved film persistency characteristics even when utilized in small amounts.

Kratz et al. U.S. Pat. No. 5,840,099 discloses a process for the selective removal of water, $CO_2$, ethane and $C_3$ hydrocarbons from gas streams, particularly a natural gas stream comprising primarily methane. The process comprises contacting the gas stream with an adsorbent material consisting exclusively of one or more compounds which are basic (i.e., compounds which, when contacted with a pH neutral aqueous solution, cause such solution to have a pH greater than 7.0) and which are mesoporous (i.e., compounds that have moderately small pores providing a surface area less than 500 $m^2/g$). Typical mesoporous adsorbents which are disclosed include zinc oxide, magnesium oxide and, in particular, activated alumina.

As demonstrated by the above discussion, many corrosion inhibitors are known in the art, and their application to liquid hydrocarbons is broad-ranging. Generally, in diesel fuel, oil-soluble corrosion inhibitors are applied. Concentrations range from about 2% to as much as 20% by volume. The inhibitor is injected as a solution through an injection quill upstream of the region where corrosion protection is required.

Generally, corrosion inhibitors are injected in the hydrocarbon stream at gas-oil separation plants to prevent corrosion from wet fuel. The inhibitor is further transported with the diesel fuel downstream ideally in a regulated and predictable manner. However, because there always exists some uncertainty as to actual injection rates of the corrosion inhibitors and to make more effective use of chemical inhibitors, manual sampling is desirable. Manual sampling assures the operator that a measureable amount of inhibitor residue is available to neutralize the corrosive compounds transported with the gas. Therefore, in order to effectively apply the proper amount of corrosion inhibitor and to limit excess residue transported along the pipeline, an effective method and apparatus for sampling must be provided. Thus, while the prior art has long taught the use of corrosion inhibitors, it has not disclosed a method or apparatus for testing to determine the presence of an excess or residue of said corrosion inhibitor(s) found in the pipelines.

The level or concentration of corrosion inhibitors remaining in a sour gas contained in a high pressure pipeline is difficult to determine analytically. Specifically, existing apparatus and methods for sampling high-pressure gas streams make it difficult to capture and analyze for the presence of corrosion inhibitors. The detection of corrosion inhibitor residue is made difficult due to such factors as aromatics content, the length of the pipeline, pipeline temperature, batch size, batch sequencing, and the like. In addition, obtaining the required samples is difficult where liquid phase corrosion inhibitors accumulate in the lower half of the pipeline. However, existing gas sampling taps and valves are typically positioned in the upper portion of the pipeline, since it is preferred to place sampling valves in the upper portion in order to avoid contact with the highly corrosive liquids. Therefore, an effective sampling method is required that will provide for the recovery of representative samples for analytical testing.

Current sampling methods in the art employ analysis of condensate withdrawn from slugcatchers. Slugcatchers are an effective source of pipeline liquids; however, they fail to provide a representative sample throughout the length of the pipeline. Recovery of non-representative samples occur because slugcatchers are generally located at the terminal points of a pipeline. In addition, slugcatchers are sometimes common to more than one pipeline. Slugcatchers have not been utilized in the art and are not an acceptable source of samples for use in analyzing for residual corrosion inhibitors, specifically imidazoline-based inhibitors, in the feedstream of a gas transmission pipeline.

Another method of trapping corrosion inhibitor residues in volatile solvents has been employed with very limited success. Gas from the pipeline is bubbled through a solvent trap containing methylene chloride or chloroform at atmospheric pressure. One drawback of this method is that gas entering the solvent trap is less likely to be representative of the gas in the pipeline. For example, liquid residing in the body of the valve could be entrained by gas rushing past the valve orifice, or conversely, liquid entrained in the gas may not stay entrained while traveling through a long conduit from the valve to the solvent trap. There are many other difficulties associated with this method, including the handling and transportation of a volatile solvent and the regulation of gas flow through the pipeline gate valve, that render this method impractical, hazardous, and unreliable.

Analytical methods that are endorsed by the manufacturers of the chemical corrosion inhibitors tend to rely on the observation of fluorescence spectra, either directly from active amine, amide or imidazoline, or from the derivatives generated from the parent amine, amide and imidazoline complexes that exhibit strong fluorescence spectra. This approach does not reveal any specific structural information about the active ingredient. The protection of the proprietary formulations of their products may be why the chemical manufacturers endorse its practice. Thus, using fluorescence methods, it may be difficult, if not impossible to distinguish between different products. A more serious shortcoming is the potential for interference from residual condensate and/or oils that bear unsaturated functional groups, which can also contribute to fluorescence.

The determination of moisture content in gaseous process streams can be utilized to indicate important process conditions both upstream and downstream of the sampling point. In many chemical plants and petroleum refineries, the exact amount of water in a process stream determines the economic return on the process. For example, catalytic reformers in refineries should be operated with a very low water content for best results.

The aqueous dew point is an important parameter in the design and operation of natural gas production, processing and transportation facilities. Without on-line moisture monitors, accurate field measurements of the aqueous dew point in bases are notoriously difficult to obtain. Commercial moisture monitors are used for specific applications, but these monitors are in fixed locations to provide process information, such as the performance of a TEG dehydration plant.

Conductivity-type moisture monitors are in common use, but also have limitations. The probe cannot be exposed to conductive liquids and can be damaged by materials that are corrosive to aluminum or aluminum oxide. This includes strongly acidic materials such as hydrogen sulfide present in natural gas streams and the primary amines used as corrosion inhibitors.

Moisture analyzers for use in the laboratory are commercially available. However, these instruments require calibration, include complex electro-mechanical systems, and require gas flow measurement apparatus when used in the field. See, for example, U.S. Pat. No. 3,405,550 and it commercial embodiment from Lockwood and McLorie, Model 100.

In view of the foregoing, there clearly exists a need for an improved method and apparatus for the sampling and detection of surface-active agents in pressurized gas streams. There is also a need in the art to provide a simple, practical and effective method for monitoring and detecting the presence of residual corrosion inhibitor compounds and/or their derivatives in a gas pipeline sample.

Therefore, it is an object of the present invention to provide a method and related apparatus for sampling sour gas streams to detect the presence of surface-active additives in those streams.

Another object of the present invention to provide a method and apparatus for measuring corrosion inhibitor residue, and more specifically, imidazoline-based inhibitors, in a hydrocarbon gas stream moving through a pipeline.

It is a further object of the present invention to provide a safe and reliable method and apparatus for analyzing a gas stream to which has been added one or more corrosion inhibitors for protection of the pipeline and fittings.

Another object of the present invention to provide a method for the sampling of residual corrosion inhibitor, such as imidazoline and its derivatives, for the purpose of optimizing the injection rate of an effective amount of such costly corrosion inhibitors.

Yet another object of the present invention is to provide an apparatus for use in existing pipeline sampling systems without requiring expensive material alterations and the installation of new sampling fittings.

Other objects, features and characteristics of the present invention, as well as the methods of operation and functions of the related elements of the invention and the combination of parts and economies of development and performance, will become apparent upon consideration of the following detailed description with reference to the accompanying drawings, all of which form a part of this specification.

SUMMARY OF THE INVENTION

The above objects and other advantages are realized by the invention which comprehends an adsorption trap designed to isolate surface-active compounds carried in a gas stream by passing a metered gas sample through a stationary porous medium consisting of activated adsorption material maintained in the body of the trap, thereafter recovering the porous medium from the trap, and subjecting it to appropriate treatment to identify any adsorbed material.

The adsorption trap of the invention is designed to remove and isolate entrained surface-active components, i.e., corrosion inhibitors or moisture, from a metered volume of gas diverted from a pressurized gas stream carried in an operating pipeline. The corrosion inhibitor active ingredient(s) can be analyzed directly after extraction, or alternatively, hydrolyzed and extracted from the adsorption material. The presently preferred adsorption material is silica gel. Other adsorption materials suitable for use in the practice of the invention include zeolites, activated alumina and other mesoporous materials.

Subsequent to the extraction of an amount of a sample sufficient to perform analytical testing. An analysis of the extracted sample can be made using gas chromatography-mass spectrometry for detecting the presence of corrosion inhibitor. The testing can also include comparative chemical analysis for distinguishing among more than one corrosion inhibitor by brand-name identification of the corrosion inhibitors based on known intrinsic differences between the spectra, or other characteristics, of the commercial products. The sample can also undergo a series of tests known in the art for determining the quantity of corrosion inhibitor present.

Where the moisture content in a saturated, two-phase gas stream is the object of the analysis, a homogenous sample of the exposed medium is prepared, preferably in a controlled atmosphere, such as a glovebox, then analyzed by thermogravimetry under inert atmosphere. Alternatively, the moisture in a silica gel sample can be determined by dehydration in a vacuum oven at about 250° and recording the mass before and after the treatment. The loss of mass between ambient temperature and 250° C. can be attributed to moisture. The difference between the loss of moisture from a sample of the activated adsorption medium and at the exposed adsorption medium, both samples having been prepared and analyzed under identical conditions, can be attributed to moisture adsorbed during the exposure to the metered volume of gas in the sample withdrawn from the pipeline.

In one preferred embodiment of the present invention, gas is passed from a hydrocarbon pipeline at high pressure through a pipeline sampling device of conventional design to an adsorption trap constructed in accordance with the invention that contains adsorption material. The flow of gas to be sampled is controlled by opening a flow control valve downstream of the trap which allows the hydrocarbon fluid to first pass through an upstream retaining member which can be in the form of a filter or screen. A downstream retaining member, which can also be in the form of a porous filter or screen, retains the adsorption material in the trap body. The fluid then contacts the adsorption material, e.g., silica gel, contained in the trap body. The silica gel acts as a chemical adsorption agent. The gas experiences a substantial pressure drop across the adsorption material in the trap and is thereafter discharged at atmospheric pressure. Preferably, the residual gas is passed through a conduit into a container of water with sufficient caustic to neutralize any hydrogen sulfide in the gas stream before being released into the atmosphere. In an alternative mode of operation, the gas is passed through a conduit connected to a sealed holding tank for subsequent disposal and/or treatment.

After a predetermined volume of gas has passed through the adsorption material in the trap, the flow is discontinued and the adsorption material is removed, as by opening a threaded joint or access port. The adsorption material is treated to desorb any surface-active compound(s) which are then subjected to analysis for identification.

The adsorption medium used in the practice of the invention should be in a physical form that creates a substantially uniform plug or bed through which the gas flows. Porosity and the length of the plug are linearly related to the gaseous flow rate through the trap in accordance with Darcy's Equation. Thus, the adsorption medium should be as close to a classic porous medium as possible. The particles should be spherical and of uniform diameter. The diameter will determine the permeability of the medium after it has settled into a closed-packed relation.

As noted above, the activated silica gel adsorbs surface-active agents, such as imidazoline inhibitors, thereby providing a means for retaining the surface-active agents in a readily accessible location. The adsorbed surface-active agent(s) can be removed from the silica gel by continuous extraction using a combination of solvents that contain sufficient moisture to hydrate the silica gel. Other adsorption materials can be used to remove and retain other types of corrosion inhibitors. The adsorption material must be capable of retaining all or most of the inhibitor and/or derivatives of the inhibitor, and must also be able to release the inhibitor when treated, e.g., with solvents, other reactants, or by heating, so that the necessary analysis can be performed.

The same type adsorption material can be used in testing for water or moisture content and corrosion inhibitors. Suitable materials include 60–100 mesh size chromatographic grade silica gel. Commercial materials are readily available in pore sizes of 60 Å and 150 Å. The larger pore size of 150 Å is preferred for corrosion inhibitor testing since it has a higher loading capacity for imidazolines. The relatively smaller 60 Å pore size is suitable for moisture testing. Materials of these two pore sizes can be blended for simultaneous moisture and corrosion inhibitor tests, or either can be used alone.

Silica gel has been found to provide a suitable adsorption medium. Although zeolites have the desired adsorption properties, commercially available zeolites have not been found that have the appropriate shape for packing.

The method and apparatus can be employed to sample a pipeline at a plurality of locations downstream of the location that additives, such as corrosion inhibitors, are injected into the feedstream to determine the proper volume of additive. The invention can also be used to measure the moisture content of a process stream in order to monitor process conditions or in volatile liquid petroleum gases (LPG), such as, liquid propane and butane.

BRIEF DESCRIPTION OF THE DRAWINGS

A further understanding of the present invention will be gained by reference to the preferred embodiments set forth in accompanying drawings in which.

DETAILED DESCRIPTION OF THE INVENTION

Figure 1A:
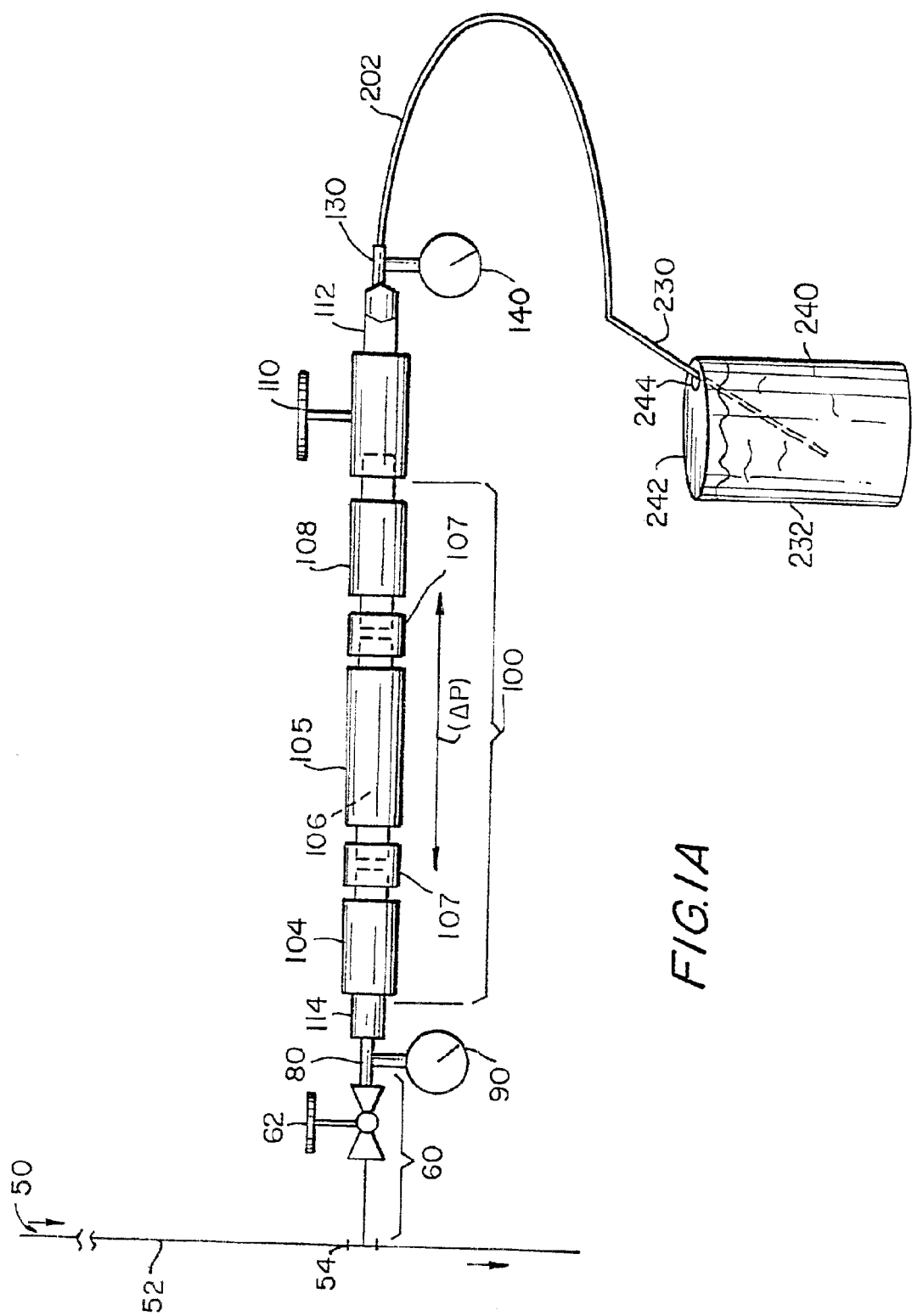
FIGS. 1A and 1B schematically illustrate alternative preferred embodiments of the adsorption trap of the invention for the detection of surface-active agents in gas streams.

With reference to FIG. 1A, there is schematically illustrated a pressurized gas pipeline 50 that is provided with a conventional gas sampling valve assembly 60 that is in communication with the interior of the pipeline. As will be understood by those familiar with the art, sampling valve assemblies are produced by a number of manufacturers; they can also be fabricated and installed by the pipeline operator. The sampling valves are positioned along the pipeline at predetermined locations to provide convenient access for sampling of the pressurized fluid passing through the pipeline. Sampling valve assembly 60 is typically mounted to communicate with the upper-half of the pipe section in order to avoid the pooling of corrosive liquid/condensate in the sampling valve assembly body.

As will be described in more detail below, if it is desired to determine the concentration of the corrosion inhibitor remaining in the gas of the pressurized pipeline at the sampling position 54, it will be necessary to determine the volume of the gas in the fluid sample removed from the pipeline. On the other hand, if the sample is to be analyzed only qualitatively to determine whether any of the corrosion inhibitor that was injected into the upstream end 52 of the pipeline 50, then the volume and conditions of the gas passing through the apparatus need not be precisely known.

Figure 1B:
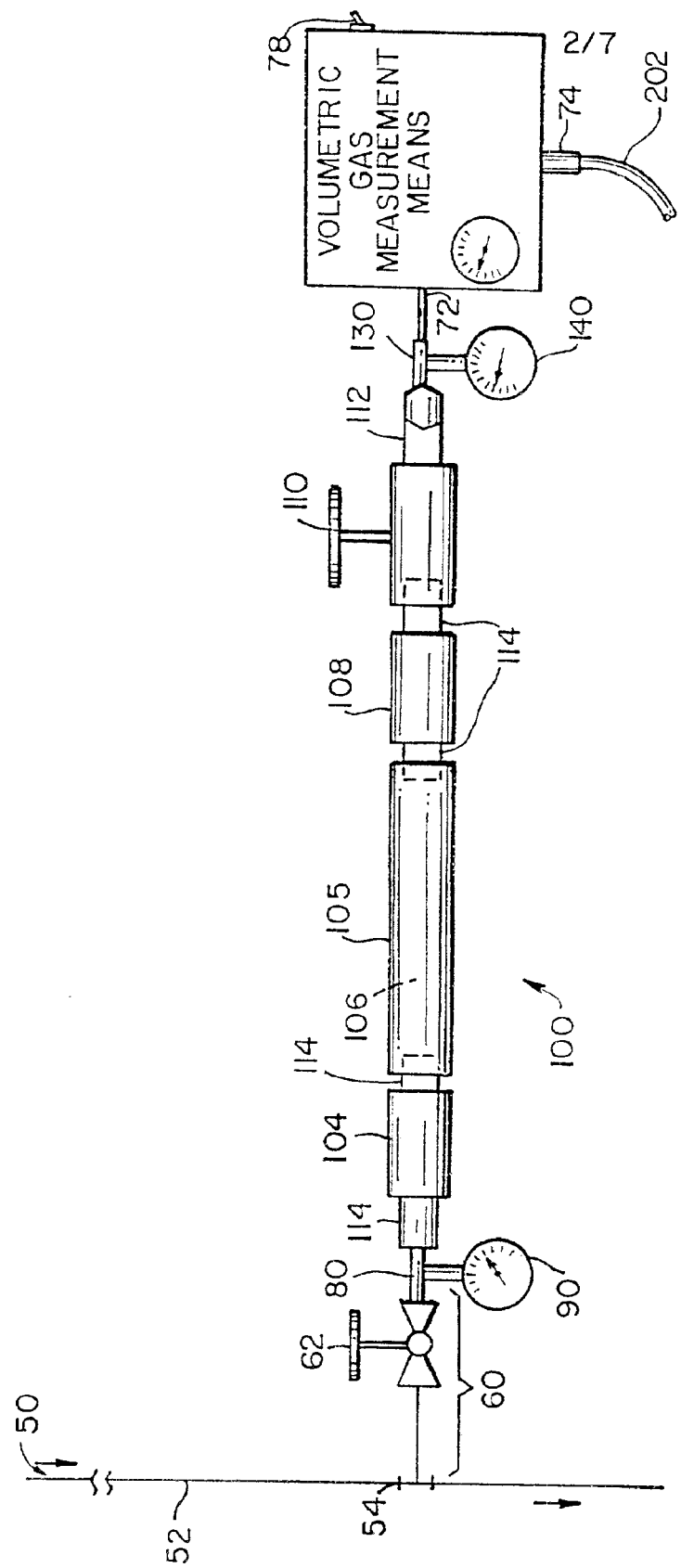

With continuing reference to FIGS. 1A and 1B, conduit 74 is secured in communication with inlet fitting 102 of adsorption trap 100. Conduit 74 is provided with upstream T-fitting 80 for mounting upstream pressure gauge 90 having an operating range that exceeds the maximum pressure of the gas stream in pipeline 50, e.g., up to 600 psi. A downstream T-fitting 130 is similarly provided with downstream pressure gauge 140, preferably having a range of 0–30 psi, that is secured to the downstream end of trap 100. The use of the gauges 90 and 140 to calculate flow rates is explained below.

It is to be understood that the obstruction of the flow of gas between the sampling point and the adsorption material in the trap is to be minimized. Thus, the shortest and most direct flow path from the pipeline to the adsorbing material is desired.

As illustrated, adsorption trap 100 includes a hollow body 105 that contains a solid active adsorption material 106 that is held in position between an upstream retaining member 104 and a downstream member 108. In a preferred embodiment, the trap body 105 is easily accessible for the removal and replacement of the adsorption material 106. The design of the body 105 should facilitate the uniform flow and distribution of the pressurized gas which passes through the material to avoid channeling or the concentration of adsorbed corrosion inhibitor that would lead to premature overloading and/or a breakthrough of gas containing corrosion inhibitor before the capacity of the adsorption material 106 has been reached.

In the embodiment illustrated, trap body 105 is cylindrical and fabricated from stainless steel. The ends are threaded to receive the retaining members 104, 108, either or both of which can be removed for removing the adsorption medium and replacing it for use in further sampling. In one preferred embodiment of the invention, the upstream retaining member 104 is fabricated to include a 440-micron gauge screen; the downstream retainer member 108 is a 90-micron 316 stainless steel mesh filter. Both retaining members are secured in place at either end of body 105 using 316 stainless steel fittings.

The selection of the type of adsorption material, e.g., silica gel, zeolite, activated alumina, is based upon the chemical composition and attraction of the material carried in the gas stream that is to be adsorbed. It is also important that the particular grade or physical configuration of the adsorption material provide a uniformly porous packing for the trap that can provide a reproducible flow rate upon the loading of each new charge of adsorption material into the trap. The flow rate characteristics of the adsorption material in a particular trap can be determined from a steady state flow rate test by passing a pressurized stream of nitrogen through the trap and measuring the volume displacement rate of gas at atmospheric pressure exiting the trap. As will be apparent to one of ordinary skill in the art, when a satisfactory type and grade of adsorption material is found by repeated calibration tests, a sufficient quantity of the material can be placed in storage for use in future tests. Since batches of materials obtained at different times from the same or different suppliers are likely to vary somewhat in their physical characteristics, it is preferable to confirm the calibration curve when a new supply of material is selected for future use.

Figure 3:
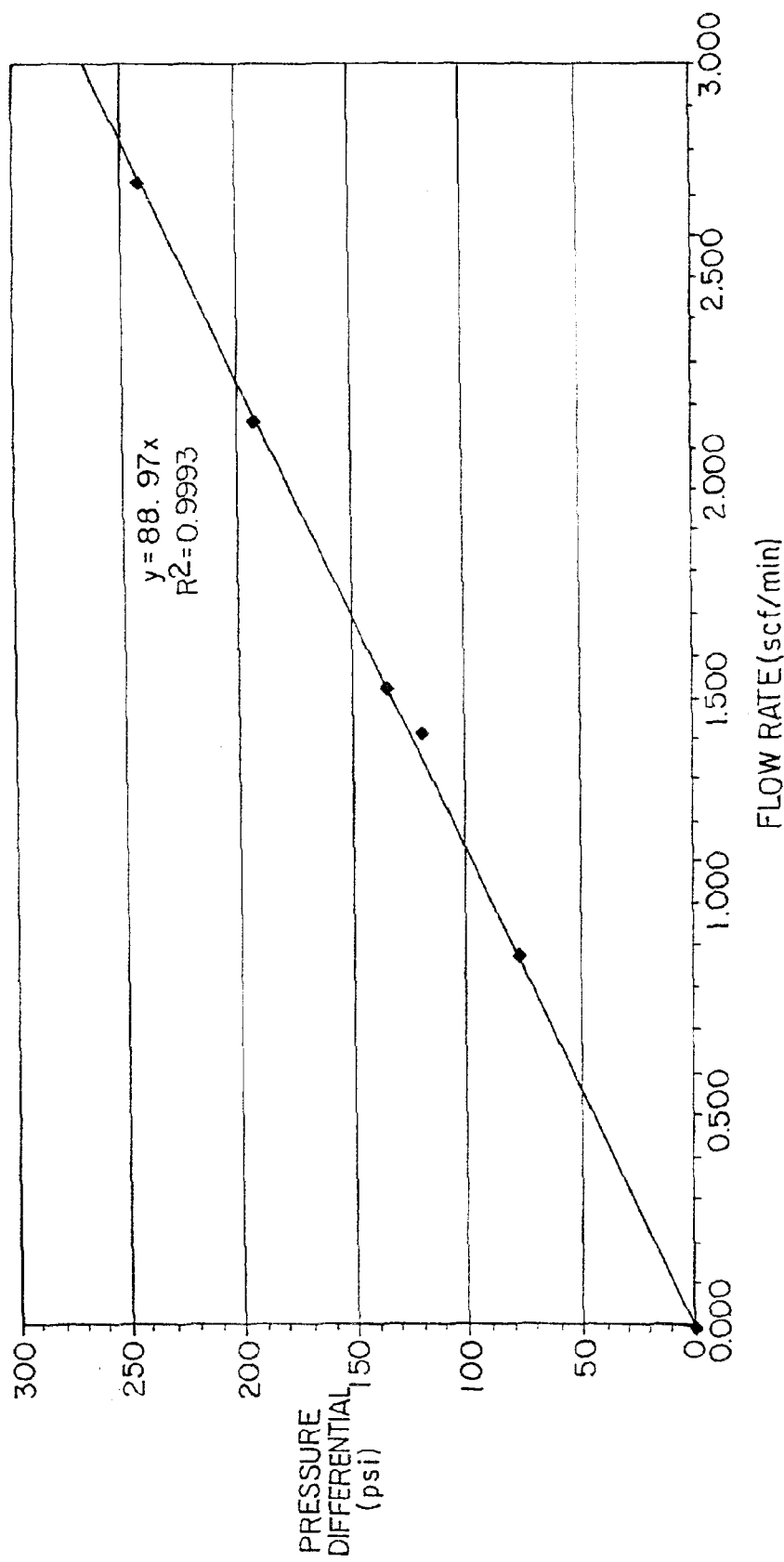
FIG. 3 is a representative calibration graph for use with the invention.

A prototype adsorption trap was charged with 60–100 mesh silica gel and calibrated by measuring the steady-state flow rate of nitrogen gas through the trap at different head pressures. As shown in FIG. 3, the linear relationship between the pressure differential and flow rate has been plotted for use as a calibration curve for determining the sampling time required to pass a give volume of gas through the apparatus. Utilizing the value of Y=88.97x, the sampling time required to collect 25 scf of gas at 60 psi head pressure is calculated as follows:

$$\Delta P = 60 - 4 = 56 \text{ psi}$$

$$56 = 88.97X (\text{scf/min})$$

$$X = 56/88.97 = 0.629 \text{ scf/min}$$

$$25 \text{ scf} \div 0.629 \text{ scf/min} = 39.7 \text{ min}.$$

Thus, in this example, a representative sample can be collected in about 40 minutes.

Figure 4:
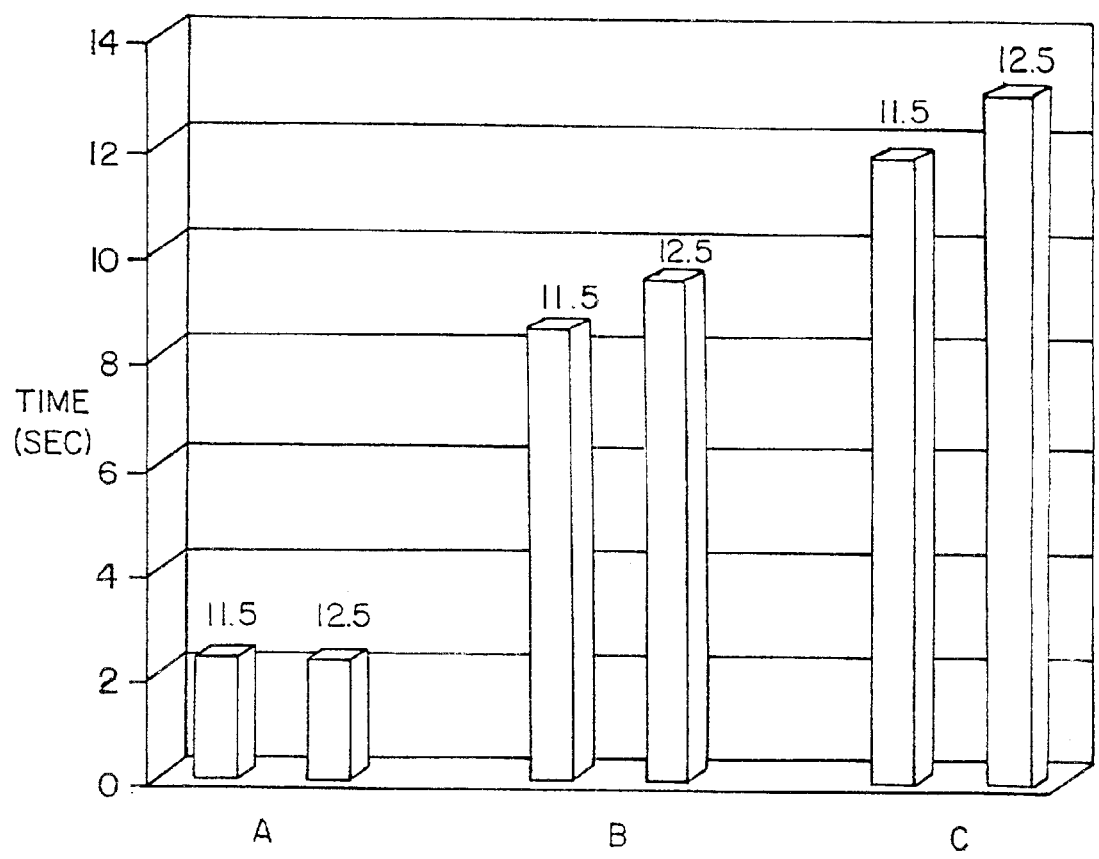
FIG. 4 is a graph depicting flow-rate data for several embodiments of the invention.

A series of flow rate tests were conducted at non-steady state conditions with the ΔP declining to zero as downstream pressure increased from zero to the head pressure with two prototype traps measuring 11.5 and 12.5 cm each charged in succession with 30–60 mesh and 60–100 mesh silica gel. The time required to pressurize a one liter cylinder to 1,000 PSIG with nitrogen gas from a regulated head pressure of 1,000 PSIG was measured. A baseline test was also conducted on the trap containing only a 90 micron mesh filter with no silica gel. The results of this series of tests are shown graphically in FIG. 4. The flow rates are expressed as the time in seconds for the two lengths, where A contains no loading, B contains 30–60 mesh and C contains 60–100 mesh silica gel. This series of tests establish that the length of the porous medium is linearly related to the flow rate as predicted by Darcy's Law as it relates to fluid flow in a porous medium. These tests also show that the porous medium is the dominant factor that affects the gas flow rate through the trap.

In a similar manner, the capacity of the silica gel to adsorb a given amount by weight of the corrosion inhibitor from the sampled gas stream can also be determined. It is important that the adsorption capacity of the silica gel in the trap not be exceeded if the concentration of the corrosion inhibitor or other test compound is to be accurately determined. On the other hand, if the method and apparatus is to be used only to indicate whether or not any amount of the corrosion inhibitor or other test compound is present, then the adsorption capacity of the silica gel and the volume of the gas sampled is not critical.

In a preferred embodiment, the chamber of body 105 is filled with 60–100 mesh silica gel packing which has the ability to adsorb surface-active agents, including corrosion inhibitors such as imidazolines. The amount or volume of silica gel placed in the adsorption trap is determined to provide an excess adsorption capacity based upon the anticipated maximum concentration of corrosion inhibitor in the gaseous sample passed through the trap. The volumetric capacity of body 105 can be varied by providing a body member of greater length and/or diameter to assure that the capacity of the silica gel is not exceeded for the expected inhibitor or moisture content in the particular volume of gas to be tested.

It has been found that a length of stainless steel pipe having an inside diameter of from 0.25 to 0.50 inches and a length of from about 3 to about 5 inches can be used for the trap body 105. In one field test, it was found that a stainless steel pipe having a diameter of 0.28 inches and packed with 60–100 mesh silica gel filling the cavity of approximately 5 inches in length between retaining members 104, 108 had flow characteristics depicted by FIG. 2 and had excess adsorption capacity for the 50 scf sample of gas tested.

With further reference to FIG. 1A, downstream retaining member 108 is fitted via conduit 114 to trap control valve 110. In the method of operating the s apparatus, control valve 110 is maintained in the closed position while the apparatus is connected to the pipeline sampling assembly 60. When all fittings have been secured, sampling access valve 62 is fully opened and the adsorption trap is equalized at essentially the same pressure as the pipeline. After noting the head pressure as indicated by the upstream pressure gauge, and marking the time, the ball value 110 is turned to the fully open position to thereby allow the sampled gas to pass through exit conduit 122 assembled to the discharge port 112 of valve 110.

As will be understood by one of ordinary skill in the art, the restrictions on flow imposed by the adsorbing media between members 104 and 108 will produce Is a significant pressure drop across trap 100. The pressure of the gas discharged from 100 as measured by the downstream pressure gauge 140 is about atmospheric pressure, i.e, 1–5 PSI above atmospheric pressure. Its pressure will depend on the length and diameter of the discharge conduit and the flow rate through trap 100.

During the sampling operation, the pressure differential between gauges 90 and 140 is noted and the flow rate determined with reference to the slope of a calibration curve prepared in advance based on the same adsorption material and trap assembly configuration.

In accordance with another embodiment of the invention illustrated on FIG. 1B, a volumetric gas measurement means 70 is positioned downstream of the discharge fitting 112 of trap 100. Gas volume measurement means 70 is prefeferably a wet-test meter. A suitable meter is sold by PAC, Petroleum Analyzer Company LP of Houston. Tex. It utilizes a liquid sealed rotating drum-type meter, and digital or analog models. A preferred model is the Singer 802. In general, the gas volume measurement means is provided with one or more gauges 76 and electronic or manual controls 78 to indicate and, if desired, record the pressure, temperature and volume of the pressurized pipeline gas passing through the device and exiting discharge conduit 202.

In one preferred embodiment, the volumetric measuring device 70 is also utilized to calibrate the trap prior to collecting the sample. Under certain conditions, it is particularly preferable to measure the gas volume while collecting the sample. For example, when the head pressure varies during the collection time interval, simultaneous volume measurement and observation is preferred. As will also be understood by one of ordinarly skill in the art, the method and apparatus can be automated to initiate and then terminate the passage of gas through the trap when a desired volume has been sampled.

Figure 2:
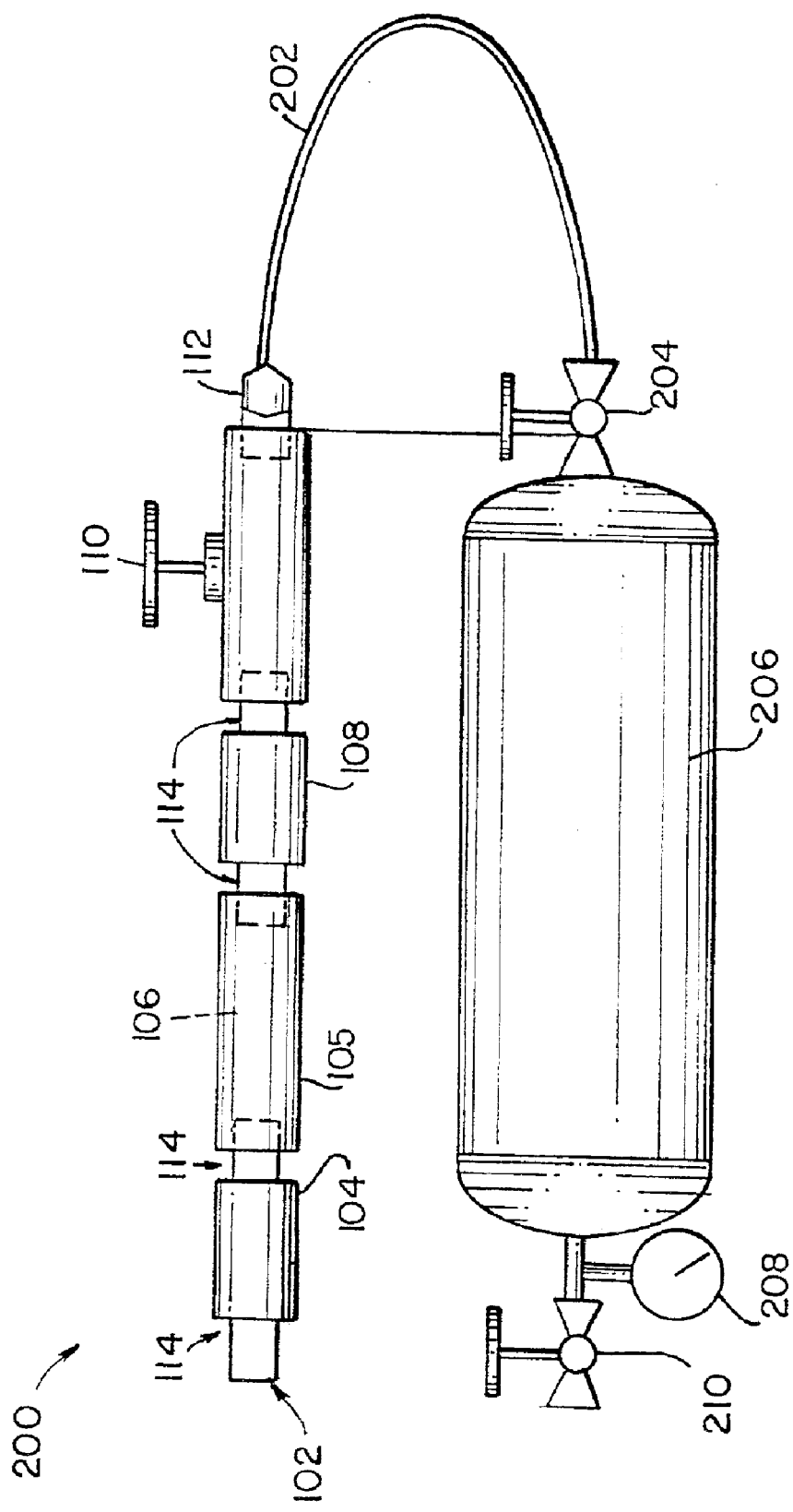
FIG. 2 schematically illustrates an alternative embodiment of the invention of FIG. 1A comprising optional components for protecting against the release of the gas sample into the atmosphere.

In an alternative embodiment illustrated in FIG. 2, the gas discharged from trap 100 is passed to a recovery reservoir 206, which can take the form of steel pressure tank fitted with appropriate control valves 204, 210 and a pressure gauge 208. For convenience, the recovery vessel 206 can be connected to discharge conduit 112 by means of a flexible high pressure hose 202. A recovery vessel permits sour gas containing hydrogen sulfide and/or other compounds that may be toxic and which cannot be released into the atmosphere at the sampling point to be retained and disposed of properly at a location established for that purpose. The recovery tank or vessel 206 has a design capacity or rating that must be greater than the maximum pressure allowed into the vessel from that will render it suitable and safe for maintaining gases at a pressure equivalent to that of the pipeline being sampled.

In the method of operating the apparatus of this further embodiment illustrated in FIG. 2, tank 206 can be evacuated to a partial vacuum in order to provide additional pressure differential; alternatively, the tank can be provided at atmospheric pressure. Valve 210, which is optional, is maintained in a closed position at all times. Valve 204 is opened after recovery conduit 202 is secured in communication with discharge fitting 112 at the discharge end of valve 110. As in the embodiment described above, sampling access valve 62 is opened and the gas trap is pressurized. Valve 110 is then opened to allow the passage of pressurized gas into reservoir tank 206 until some suitable fraction of the head pressure, preferably less than 50%, has been reached, at which time valve 110 is closed.

As will be apparent, it is much more efficient to fill the tank to some fraction of the head pressure rather than to fill the tank to 100% of the pipeline pressure, since the flow rate begins decreasing immediately with the decrease in pressure differential across assembly 100. A high flow rate should be maintained in order to divert entrained liquid droplets into the gas stream leading to the adsorption trap. It is also important to maintain the pressure differential across the adsorption material at as high a level as possible. This will promote condensation as the saturated gas moves to lower pressure. The time to collect a sample of comparable size can be minimized by partially evacuating the tank to below atmospheric pressure.

As will be understood by one of ordinary skill in the art, the use of a recovery tank of known volume which includes a pressure gauge 208, can be used in place of gas measurement means 70 to withdraw a known volume of gas from the pressurized pipeline. In this method of operation, the amount of gas admitted into recovery tank 206 can continue until the pressure in the tank reaches a predetermined level corresponding to the desired volumetric sample size, at which point the flow of sampled gas is discontinued.

The following example is illustrative of the method of the invention under conditions typically encountered in the field.

EXAMPLE 1

A sour gas pipeline is sampled for the presence of corrosion inhibitor and moisture at a gas vent located approximately two kilometers from the point of injection of the corrosion inhibitor. A stainless steel adsorption trap assembly is prepared in accordance with the apparatus and method described above. The section of pipeline has a gas vent at about the three o'clock position.

Prior to attaching the adsorption trap 100 and related apparatus, the vent valve 62 is purged to remove any residual liquids that may have accumulated in the valve body. The vent valve opening is cleared of any debris or liquid residues and is connected to the adsorption trap as shown in FIG. 1A.

Prior to sampling, an aqueous solution of about 5 gallons of water containing approximately 25 grams of $Na_2CO_3$ (soda ash) is prepared for every 50 scf of gas that will be vented. This concentration is sufficient to neutralize hydrogen sulfide at a level of 5000 ppm. Alternatively, 15 g of NaOH can be used in place of the soda. The container 240 of neutralizing solution 232 is placed conveniently to receive the low pressure gas discharged downstream of the trap assembly. The tubing 230 at the end of the high pressure hose is secured in position for discharge into the neutralizing solution through an opening 244 in the cover 242. The cover prevents splashing, and permits the vented gas to escape freely.

With the ball valve 110 on the adsorption trap in the closed position, the vent valve 62 is opened, slowly at first while listening for leaks, and then completely, to the fully open position. The ball valve on the adsorption trap is opened for the amount of time that has previously been determined to deliver the desired volume of gas sample. This time can be calculated from a calibration plot based on the pressure differential across the adsorption trap in accordance with the method described above.

In order to proceed with the analysis of the adsorption material 106 in body 105, the gas sampling access valve 62 is closed, as is valve 110, and in the case of the second alternative embodiment, valve 204 is also closed. Residual pressure in the conduit downstream from 110 is preferably reduced to atmospheric. In the second embodiment, this can be done by slowly opening the high-pressure connection on the conduit. The adsorption trap is then depressurized by briefly opening, then closing valve 110 while maintaining valve 62 in the closed position. The apparatus can then be separated from valve 62 for analysis of the adsorbed material typically in a laboratory facility.

If the adsorption trap has been used to retain imidazoline-type corrosion inhibitor compounds, the inhibitor compounds can be desorbed from adsorbing media such as silica gel by continuous extraction under conditions that favor hydrolysis of the imidazoline. It is desirable to remove residual hydrocarbons from diesel and/or crude oil carryover which can interfere with the characterization and identification of the imidazolines or with the amides derived from imidazolines by various analytical methods. Less surface-active hydrocarbons can be first removed from the silica gel by eluting with solvents such as the hexanes, toluene or methylene chloride at room temperature without removing imidazolines.

Recovery of Imidazolines from Silica Gel

The removal of imidazolines adsorbed on silica gel requires more severe conditions and/or the use of solvents that compete with imidazolines for the active sites on the silica gel. Tertiary amines can be utilized to displace the imidazolines from the silica gel. However, a preferred method is to hydrolyze the imidazoline to its corresponding amide. This method is preferred because of the relative ease in removing the reagent by evacuation after the extraction is complete. In the following examples, the trap has been set up and the pipeline sampled, as described above and the silica gel adsorbent recovered from the trap.

EXAMPLE 2

Using a 90:9:1 mixture of toluene, methanol and water, the later preferably being a 2% aqueous NaOH solution, the imidazoline, is hydrolyzed to its corresponding amide, and is extracted from the silica gel by continuous extraction for 6 hours in a Soxhlet apparatus. After removal of the solvents invacuuo, the amide residue was dissolved in a small quantity of methylene chloride and then transferred through a solvent-resistant (PTFE) micro-filter into a glass syringe. The filtered amide solution was then transferred into a small vial and evaporated to a minimum volume. Since the amide is far less surface-active than the parent imidazoline, it can be analyzed by gas chromatography-mass spectrometry (GC-MS) using a DB-1 column and electron impact at 70 ev. The characteristic peaks can be identified based upon standards and/or comparative tests on known commercial products that have been used in the pipeline, as described more fully below.

The solvent(s) containing any materials removed from the silica gel are further processed and analyzed by conventional means. In the case of samples to be analyzed for the presence of one or more imidazolines and/or their derivatives, the amide hydrolysis product is readily detected by gas chromatography-mass spectrometry by monitoring the peak that is characteristic of the compound of interest.

As will also be understood by those of ordinary skill in the art, characteristic spectra can be prepared from known commercial samples to provide a characterizing reading. It has been found that amides generated from corrosion inhibitors of the same general type, but sold by different commercial manufacturers, may exhibit GC-MS data which are sufficiently distinctive so that the active ingredients in the downstream gas pipeline can be identified as to their source.

Figure 5A:
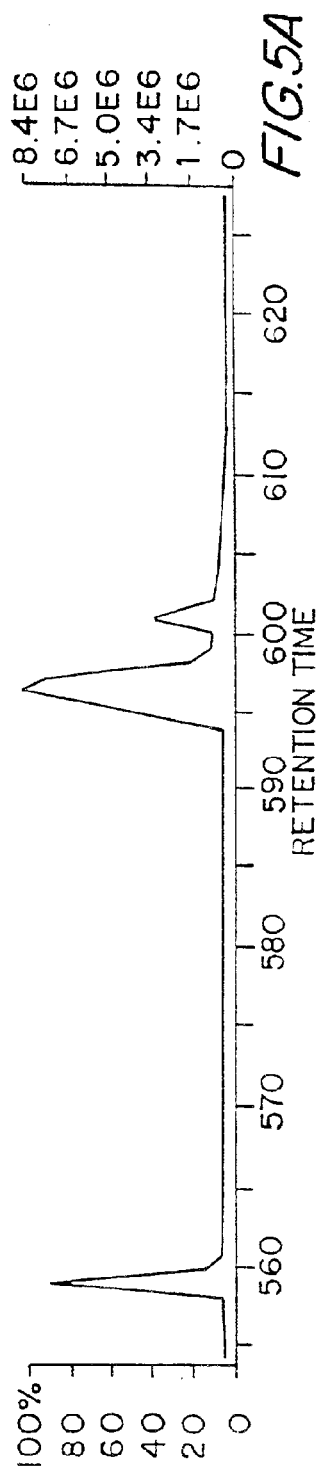
FIGS. 5A, 5B and 5C provide a graphical comparison of the spectral analysis of a known corrosion inhibitor recovered from the adsorption trap of the invention, and the condensate from a prior art slugcatcher, with the spectrum of a known inhibitor.
Figure 5B:
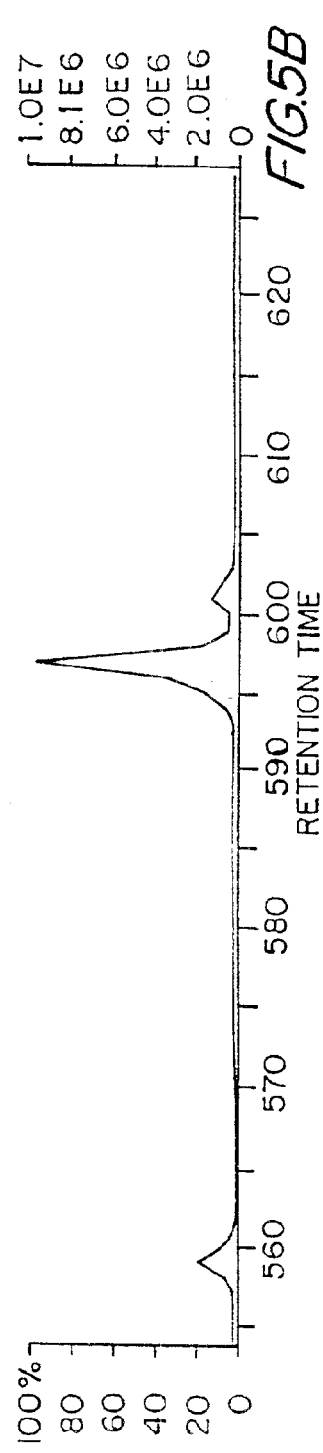
Figure 5C:
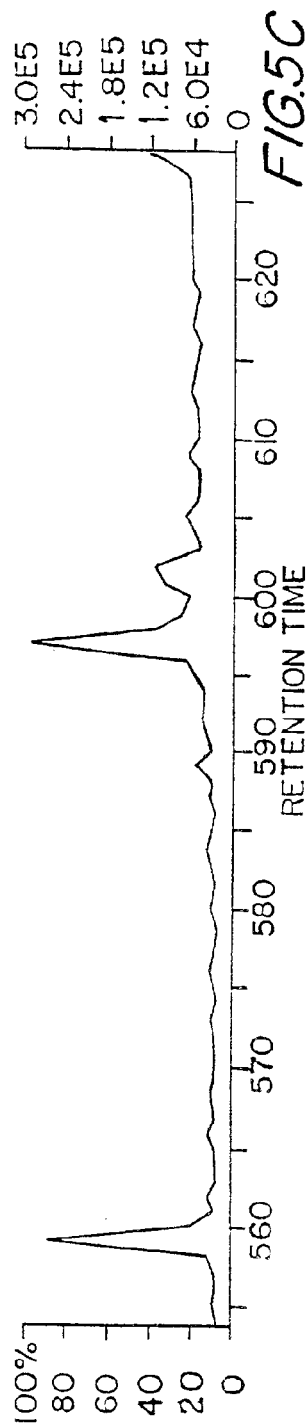

With reference to FIGS. 5A, 5B and 5C, there are shown comparative spectra prepared from three different samples. The horizontal axis on all three plots is to the same scale and represents retention time in accordance with standard recording protocol; the right side vertical axis is ion intensity. FIG. 5A was prepared from a sample of pure commercial corrosion inhibitor marketed under the brand name "A", and is used as a standard for comparison. FIG. 5B is a spectra prepared from a liquid sample taken from a slugcatcher residue and is based upon 50 mL of condensate. FIG. 5C is a sample prepared in accordance with the method and using the apparatus of the invention described above, the sample having been recovered from 50 SCF of gas. As can be seen, the qualitative information provided by FIG. 5C very closely matches that of the commercial standard "A", and more closely resembles the standard than that derived from the slugcatcher condensate represented by FIG. 5B. These comparative spectra establish the superiority of the method and apparatus of the invention over that known to the prior art.

It is only necessary to remove less polar residual hydrocarbons from the silica gel before attempting to extract the imidazoline if they are known to interfere with the detection of the imidazoline or its hydrolysis products. When GC-MS is used as the analytical method, minor amounts of the residual diesel or crude oil carry-over will usually not interfere with the detection of the amide generated from the imidazoline. However, plasticizer can interfere with the analysis. It is very common to find traces of plasticizer in solvents unless they have been thoroughly purified to eliminate contaminants. It is also very easy to introduce significant traces of plasticizer in thoroughly purified solvents just by handling them. Therefore, attempting to elute minor contaminants from the silica gel before extracting the adsorbed imidazolines may not be necessary and, in some cases, may actually introduce interfering compounds.

In a second preferred embodiment, the adsorption trap of the invention is used to extract measurable quantities of moisture from the gas stream sampled thereby providing a reliable and inexpensive alternative to other moisture monitors. The method and set up of the apparatus is substantially the same as that described above. The adsorption material is preferably a 60–100 mesh silica gel with a 60 Å pore size. The following example illustrates a method for calculating the moisture extent of the adsorption material.

EXAMPLE 3

The silica gel adsorption material is removed from the trap and weighed. If the presence of volatile hydrocarbon compounds in the adsorption trap medium is thought to be negligible, then the silica gel sample is dehydrated by heating to about 250° C. The mass of the silica gel sample is recorded before and after heating/evacuation. The weight difference is attributed to moisture. The concentration of moisture in the original gas sample can then be determined based on the known volume of gas that passed through the trap.

The method of the invention can also be employed to determine moisture content and corrosion inhibitor from the same sample, or preferably, for a plurality of samples. The amount or concentration of water in a wet, sour gas stream can be expected to be many times that of any corrosion inhibitor present. In the practice of the method for simultaneous sampling, the adsorption material must not be overloaded, i.e., no breakthrough or saturation should occur. A substantially larger volume of adsorption material may therefore be required for the simultaneous sampling, than if only the presence of corrosion inhibitor is to be determined.

In order to assure an accurate measure of moisture content, it is preferred to obtain at least three consecutive samples at different exposures that span a range of moisture content, to determine the value of each sample and confirm that a linear relationship exists between the gas volume of the sample and moisture content of the exposed adsorption material.

EXAMPLE 4

The following method is employed where the adsorption material sample has been exposed to both moisture and corrosion inhibitor, and values of both components are desired. A flask designed for inert atmosphere and vacuum procedures, such as a Schlenk flask is utilized. The construction and arrangement of the apparatus for use in the practice requires that the moisture be separated from the silica gel without also removing the trapped volatile hydrocarbons.

Figure 6:
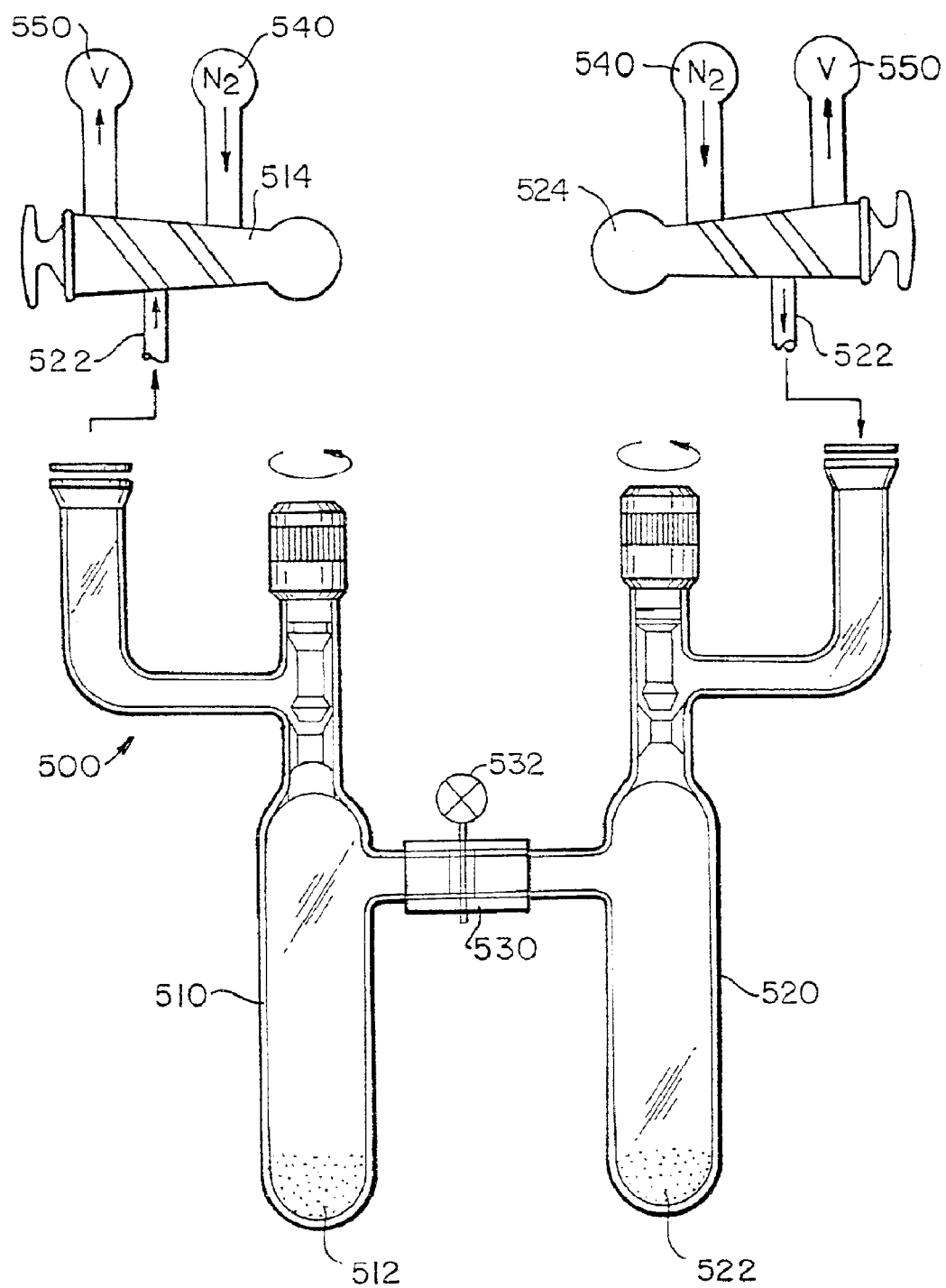
FIG. 6 illustrates one embodiment for the determination of the moisture content of adsorption material for use in the practice of the invention.

As schematically illustrated in FIG. 6, the exposed adsorption material 106 is loaded into a first chamber 510 of mated Schlenk flask assembly 500 under a dry nitrogen atmosphere and weighed on a milligram balance. A second mating chamber 520 of the flask assembly is provided with a strong desiccant 522, such as phosphorous pentoxide. The two flasks 510, 520 are connected, as with vacuum tubing 530 and, optionally, valve 532; alternatively, a rubber septum can be positioned between the flasks to provide a seal upon their separation. Each flask is also fitted with a 3-way valve 514, 524, respectively, that permits the contents of the flasks to be subjected to a vacuum V 550, or a source of inert gas 540, such as nitrogen.

The flask 510 containing the adsorption material is cooled to about 80° K with liquid nitrogen and the entire apparatus is evacuated, as via vacuum lines 514, 524. The valve 532 between the flasks is opened while the flask 510 containing the adsorption material 512 is heated to about 250° C. for about one hour, after which the flask 510 is again cooled with liquid nitrogen. Once cooled, flask 510 containing the adsorption material is isolated, allowed to warm to room temperature and then filled with dry nitrogen. The flask and its now-dehydrated contents are again weighed, the difference in weight representing that of the water adsorbed from the gas sample.

The dried adsorption material sample containing corrosion inhibitor is removed from flask 510 and subjected to the procedure of Example 2, above in order to determine the concentration of corrosion inhibitor present.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all alternative methods of the invention. It will be apparent to those of ordinary skill in the art that numerous adaptations can be made without departing from the spirit and the principles of the invention. The scope of the invention, therefore, shall be defined solely by the following claims.

I claim:

1. Apparatus for use in detecting a surface-active corrosion inhibitor additive in a petroleum gas sample withdrawn from a generally inaccessible pressurized feedstream traveling in a high pressure gas transmission pipeline through standard gas sampling means that is in communication with the pressurized feedstream to withdraw the gas sample out of line of the pressurized feedstream, the apparatus comprising:
   a. a pre-calibrated compact and manually portable adsorption trap in fluid communication with the standard gas sampling means out of line of the pressurized feedstream, the adsorption trap containing a predetermined charge of a uniformly porous and closely-packed plug of adsorption material that selectively removes from the gas sample entrained surface-active corrosion inhibitor contacting the adsorption material, and that reduces the pressure to substantially atmospheric pressure at the downstream end of the trap, the adsorption trap having an upstream inlet port for receiving the gas sample from the sampling means at the feedstream pressure and a downstream outlet port for discharging the gas sample at substantially atmospheric pressure after passing through the adsorption material, the charge of adsorption material being retained in a trap body and having uniform gas flow and distribution properties, the adsorption material being fixedly retained between the inlet and outlet ports, said trap having access means for removing and replacing the adsorption material; and
   b. at least one control valve positioned downstream of the trap body for establishing a uniform gas flow through the adsorption trap body.

2. The apparatus of claim 1, wherein the adsorption trap includes a hollow cylindrical body member for receiving and maintaining a predetermined volume of the adsorption material between the gas inlet port and gas outlet port, thereby providing uniform flow and distribution of the gaseous sample through the body.

3. The apparatus of claim 1 further comprising porous retention means in contact with the adsorption material contained in the body for retaining the adsorption material at a fixed position in the body of the trap.

4. The apparatus of claim 3, wherein the porous retention means comprises an upstream retainer positioned proximate the inlet port and a second retainer positioned proximate the outlet port.

5. The apparatus of claim 3, wherein the porous retention means extend across the flow path of the gaseous sample passing through the adsorption trap.

6. The apparatus of claim 3, wherein the adsorption trap body and porous retention means are generally cylindrical and are provided with threads for mating engagement.

7. The apparatus of claim 1, wherein the at least one control valve downstream of the trap outlet port includes a ball valve.

8. The apparatus of claim 1 which further comprises flow-rate measurement means for measuring the volumetric flow-rate of the gaseous sample through the trap.

9. The apparatus of claim 8, wherein the flow-rate measurement means comprises a first pressure gauge located between the gas sampling means and the adsorption trap and a second pressure gauge located downstream of the outlet port.

10. The apparatus of claim 8, wherein the flow-rate measurement means is a wet-test meter located downstream of the trap.

11. The apparatus of claim 10, wherein the meter includes a rotating drum and digital data display means.

12. The apparatus of claim 1, wherein the trap includes at least one threaded joint to provide access to the interior of said trap body.

13. The apparatus of claim 1, wherein the adsorption trap is constructed of an alloy metal.

14. The apparatus of claim 13, wherein the alloy metal is stainless steel.

15. The apparatus of claim 1, wherein the adsorption material is selected from the group consisting of silica gel, activated alumina and zeolites.

16. The apparatus if claim 1, wherein said surface-active corrosion inhibitor comprises an imidazoline-based inhibitor.

17. The apparatus of claim 16, wherein the adsorption material is silica gel.

18. A compact manually portable adsorption trap assembly for use in connection with a standard gas collection apparatus, said apparatus being in fluid communication with a high pressure gas stream in a generally inaccessible gas transmission pipeline, the trap comprising:
   a trap body having an inlet port and an outlet port, a predetermined charge of a uniformly porous and closely-packed plug of adsorption material fixedly positioned in the trap body between the inlet and outlet ports, said absorption material having uniform gas flow and distribution properties, whereby the pressure of the as is reduced to substantially atmospheric pressure at the outlet port and the volumetric flow rate of a pressurized gas stream through the charged trap body is proportional to the time that gas is passed through the charged trap body; and access means for removing and replacing the adsorption material in the body of the trap;

and at least at one control valve positioned downstream of the trap body for establishing a uniform flow of gas through the adsorption trap body.

19. The trap of claim 18 further comprising porous retention means for fixedly retaining the adsorption material in the body of the trap.

20. The trap of claim 19, wherein the porous retention means comprises an upstream retainer positioned proximate the inlet port and a downstream retainer positioned proximate the outlet port.

21. The trap of claim 19, wherein the porous retention means extend across the flow path of the gaseous sample passing through the adsorption trap.

22. The trap of claim 19, wherein the adsorption trap body and porous retention means are generally cylindrical and are provided with threads for mating engagement.

23. The trap of claim 18, wherein the access means is a threaded joint in communication with the interior of said trap.

24. The trap of claim 18, wherein the adsorption trap is constructed of an alloy metal.

25. The trap of claim 24, wherein the alloy metal is stainless steel.

26. The trap of claim 18, wherein the adsorption material is selected from the group consisting of silica gel, activated alumina and zeolites.

27. A method for determining the presence of one or more surface-active compounds in a gaseous sample withdrawn from a generally inaccessible pressurized gaseous petroleum feedstream through standard gas sampling means, the method comprising:
(a) providing a compact, manually portable adsorption trap assembly that comprises a trap body having an inlet port for receiving a sample of gas withdrawn from the pressurized feedstream through a standard gas sampling means and an outlet port for discharging the gaseous sample at a substantially reduced pressure, said trap body containing a predetermined charge of a uniformly porous adsorption material that adsorbs and retains surface-active compounds upon contact with the gaseous sample, said charged trap body having uniform gas flow and distribution characteristics and access means for removing the adsorption material from the trap body and
(b) a flow control valve in fluid communication with and downstream of the trap;
securing the adsorption trap assembly to the standard gas sampling means;
(c) closing the flow control valve downstream of the trap body;
(d) admitting pressurized gas from the feedstream through the sampling means into static contact with the adsorption material in the trap body;
(e) opening the flow control valve, thereby admitting a high-pressure gaseous sample from the feedstream through the adsorption trap assembly to contact the adsorption material;
(f) discharging the gaseous sample from the trap at a substantially reduced pressure;
(g) closing the flow control valve after a predetermined period of time, thereby discontinuing the passage of pressurized gas through the trap assembly;
(h) closing the sampling means to isolate the trap from the pressurized feedstream;
(i) removing the adsorption material from the trap;
(j) separating any adsorbed compounds from the adsorption material and recovering any adsorbed compounds present in the form of at least one analyzable sample; and
(k) analyzing the at least one recovered sample for the presence of one or more surface-active compounds.

28. The method of claim 27 where the petroleum feedstream is contained in a pipeline and the sampling means includes a gas sampling valve, and the method includes securing the adsorption trap assembly to the gas sampling valve.

29. The method of claim 28 which includes the further steps:
(l) adding a surface-active corrosion inhibitor having known physical characteristics to said pipeline upstream of said sampling valve;
(m) comparing the physical characteristics of any surface-active compounds analyzed in step (k) with those of the added corrosion inhibitor; and
(n) recording the results of the comparison.

30. The method of claim 29, wherein the added corrosion inhibitor is an imidazoline and the adsorption material is silica gel.

31. The method of claim 27, wherein the separation of any adsorbed compounds from the adsorption material includes the steps of:
contacting the adsorption material with at least one other reactive compound that converts any adsorbed compound to a related derivative chemical compound; and
desorbing the related chemical compound.

32. A method for determining the presence of one or more surface-active compounds in a gaseous stream passing through a generally inaccessible pressurized gas transmission pipeline that is provided with means for passing a sample of the gas stream out of line of the transmission pipeline that includes a standard structure for removing the gas sample, the method comprising the steps of:
(a) providing a pre-calibrated compact and manually portable gas sampling adsorption trap assembly that includes
(i) a portable trap body,
(ii) a uniformly porous packed bed of adsorption material selected from the group consisting of silica gel, zeolites and activated alumina, the packed bed being fixedly positioned in the trap body and having uniform gas flow and distribution characteristics, and
(iii) at least one control valve positioned downstream of the trap body for establishing a uniform flow of gas through the adsorption trap body;
(b) passing for a predetermined period of time, using the means for passing, a volume of the gas sampled through the adsorption trap assembly and in contact with the adsorption material;
(c) recovering from the adsorption material any compounds adsorbed during contact with the gas sample; and
(d) testing any compound recovered from the adsorption material for the presence of the one or more surface-active compounds.

33. The method of claim 32 which includes the further steps:
(a) adding one or more surface-active compounds to the pipeline upstream of the sampling assembly, each compound having at least one known physical characteristic;
(b) comparing the physical characteristics of any surface-active compounds tested with the at least one known physical characteristic of the one or more surface-active compounds added to the pipeline; and
(c) recording the results of the comparison.

34. The method of claim 33, wherein the surface-active compounds added are corrosion inhibitors and the bed is packed with silica gel.

35. The method of claim 34, wherein the recovery of any adsorbed compounds includes the additional steps of:
contacting the adsorption material with at least one other reactive compound that converts any adsorbed compound to a related derivative chemical compound; and
desorbing the related chemical compound.

36. The method of claim 35, wherein one or more imidazoline corrosion inhibitors are added to the pipeline and any adsorbed imidazoline is converted into a derivative amide in an hydrolysis reaction.

37. The method of claim 32 that includes:
repeating steps (a) through (d) in at least one other location on the same pipeline; and
comparing the results of the test results obtained at the second and any additional locations.

38. The method of claim 32 hat further comprises precalibrating the trap assembly by measuring the volumetric flow rate of nitrogen volume gas passing through the trap at one or more test pressures approximating the pressure of the gas in the transmission pipeline.

39. The method of claim 32 further comprising:
(e) providing a volumetric flow measurement means;
(f) securing the flow measurement means in fluid communication with the adsorption trap;
(g) measuring and recording the volume of the gas passing through the trap at one or more test pressures.

* * * * *